United States Patent
Niazi et al.

(10) Patent No.: US 12,053,512 B2
(45) Date of Patent: Aug. 6, 2024

(54) METHOD OF VALIDATING THE TRIGGERING OF AN IMMUNE RESPONSE TO A NEOEPITOPE OF A TUMOR WITH T-CELLS

(71) Applicants: NantBio, Inc., Culver City, CA (US); Nant Holdings IP, LLC, Culver City, CA (US); NantOmics, LLC, Culver City, CA (US)

(72) Inventors: Kayvan Niazi, Culver City, CA (US); Nicholas J. Witchey, Culver City, CA (US); Stephen Charles Benz, Culver City, CA (US); Shahrooz Rabizadeh, Culver City, CA (US)

(73) Assignees: NantBio, Inc., Culver City, CA (US); Nant Holdings IP, LLC, Culver City, CA (US); NantOmics, LLC, Culver City, CA (US)

( * ) Notice: Subject to any disclaimer, the term of this patent is extended or adjusted under 35 U.S.C. 154(b) by 1065 days.

(21) Appl. No.: 16/465,675

(22) PCT Filed: Dec. 5, 2017

(86) PCT No.: PCT/US2017/064728
§ 371 (c)(1),
(2) Date: May 31, 2019

(87) PCT Pub. No.: WO2018/106699
PCT Pub. Date: Jun. 14, 2018

(65) Prior Publication Data
US 2021/0113672 A1 Apr. 22, 2021

Related U.S. Application Data

(60) Provisional application No. 62/431,817, filed on Dec. 8, 2016.

(51) Int. Cl.
| | | |
|---|---|---|
| *G01N 33/50* | (2006.01) | |
| *A61K 39/00* | (2006.01) | |
| *G01N 33/569* | (2006.01) | |

(52) U.S. Cl.
CPC ........ *A61K 39/0011* (2013.01); *G01N 33/505* (2013.01); *G01N 33/5052* (2013.01); *G01N 33/56977* (2013.01); *A61K 2039/5158* (2013.01); *A61K 2039/605* (2013.01); *A61K 2039/6081* (2013.01)

(58) Field of Classification Search
None
See application file for complete search history.

(56) References Cited

U.S. PATENT DOCUMENTS 10,532,089 B2 * 1/2020 Benz ................ G16B 20/20
2002/0098527 A1 7/2002 Shitara et al.

FOREIGN PATENT DOCUMENTS

| WO | 2011/159877 A2 | 12/2011 |
| WO | 2016/191545 A1 | 12/2016 |
| WO | 2020/096640 A2 | 5/2020 |

OTHER PUBLICATIONS

Linnemann et al (Nature Medicine, Jan. 2015, published online Dec. 22, 2014, 21(1): 81-86) (Year: 2015).*
Jiang et al (Cell Death and Disease, 2015, 6, e1792, pp. 1-9) (Year: 2015).*
Schurich et al (PLOS Pathogens 2013, 9(3) e1003208, pp. 1-12) (Year: 2013).*
Colluru and McNeel (Oncotarget, Sep. 21, 2016, 7(42): 67901-67918) (Year: 2016).*
Schumacher and Schreiber (Science, Apr. 3, 2015, 348(6230): 69-74) (Year: 2015).*
Lizee et al (Human Gene Therapy, 2004, 15: 393-404) (Year: 2004).*
Merriam-Webster (2023, merriam-webster.com/dictionary/therapeutic, pp. 1-14) (Year: 2023).*
Spranger, S (Int. Immunol. 2015, 28(8): 383-391) (Year: 2015).*
Beatty and Gladney (Clin. Canc. Res. 2014, 21(4): 687-692) (Year: 2014).*
Kerkar and Restifo (Cancer Res. 2012, 72(13): 3125-3130) (Year: 2012).*
Kalos and June (Immunity, 2013, 39: 49-60) (Year: 2013).*
Tran et al (Nature Immunology, published online Feb. 17, 2017, 18(3): 255-262) (Year: 2017).*
Kamphorst et al (PNAS, May 9, 2017, 114(19): 4993-4998) (Year: 2017).*
Trainor; et al., "Rethinking clinical delivery of adult stem cell therapies", Nature Biotechnology, 2014, vol. 32, No. 8, pp. 729-735.
ISA/US, PCT International Search Report and Written Opinion, mailed Apr. 25, 2018, which were issued in connection with PCT/US17/64728 (15 pages).
Hung, Kenneth; et al., "The Central Role of CD4+ T Cells in the Antitumor Immune Response", J Exp Med Dec. 21, 1998; 188 (12): 2357-2368.

* cited by examiner

*Primary Examiner* — Michael Szperka
*Assistant Examiner* — Marianne DiBrino
(74) *Attorney, Agent, or Firm* — Martin Fessenmaier; Umberg Zipser LLP

(57) ABSTRACT

The invention provides a method of validating the therapeutic composition that is prepared for immunotherapy of a tumor or cancer. The method includes, triggering of an immune response to a neoepitope of a subject's tumor by: a) obtaining neoepitope sequence data from the tumor of a subject; b) obtaining immune competent cells; c) using the neoepitope sequence data to generate a neoepitope presentation system; d) triggering an immune response by contacting the immune competent cells with the neoepitope presentation system; and e) quantifying the triggering of the immune response from the contacted immune competent cells.

11 Claims, No Drawings

METHOD OF VALIDATING THE TRIGGERING OF AN IMMUNE RESPONSE TO A NEOEPITOPE OF A TUMOR WITH T-CELLS

CROSS-REFERENCE TO RELATED APPLICATIONS

This application is a 371 of PCT/US2017/064728, filed Dec. 5, 2017, which claims benefit of U.S. Provisional Patent Application No. 62/431,817 filed on Dec. 8, 2016.

FIELD OF THE INVENTION

The field of the invention relates to methods of validating the triggering of an immune response to a neoepitope of a tumor.

BACKGROUND OF THE INVENTION

The background description includes information that may be useful in understanding the present invention. It is not an admission that any of the information provided herein is prior art or relevant to the presently-claimed invention, or that any publication specifically or implicitly referenced is prior art.

All publications, patents, and patent applications recited herein are incorporated by reference to the same extent as if each individual publication, patent, or patent application were specifically and individually incorporated by reference. Where a definition or use of a term in an incorporated publication, patent, or patent application is inconsistent or contrary to the definition of that term provided herein, the definition of that term provided herein applies and the definition of that term in the reference does not apply.

Despite recent advances in the diagnosis and treatment of cancer, many types of cancers remain difficult to drive into long term remissions. Currently, one promising avenue of research is the individualized therapy of cancers. The concept is based on the observation that each cancer, in each individual patient or subject, is in some ways unique, and if the therapy is tailored to address or target the specific damaged genetic and/or regulatory cellular pathway in a specific tumor, the prospects of a successful treatment will be enhanced. Thus, anticancer vaccines, or other types of immune therapies for eliciting an immune response to a subject specific tumor, or anticancer pharmaceutical regimens tailored to a specific tumor found in a specific individual subject, are under investigation and have shown some early dramatic successes in improving clinical outcomes for subjects diagnosed with cancer.

However, individualized, subject specific anticancer treatments, including personalized vaccines based on cancer neoepitopes, are very costly in time, money, laboratory resources, and the efforts of the individual subjects receiving the treatment. Thus, there remains a longstanding need in the art for cost effective, efficient and relatively rapid methods of verifying or validating the effectiveness of a proposed individualized anticancer immunotherapy, in eliciting an antitumor immune response in a subject.

SUMMARY OF THE INVENTION

Broadly, the invention includes a method of validating the triggering of an immune response to a neoepitope of a first subject's tumor, comprising:

a) obtaining neoepitope sequence data from the tumor of the first subject;
b) obtaining immune competent cells;
c) using the neoepitope sequence data to generate a neoepitope presentation system;
d) triggering an immune response by contacting the immune competent cells with the neoepitope presentation system; and
e) quantifying the triggering of the immune response from the contacted immune competent cells.

In several alternative aspects, the immune competent cells, or the cells for the neoepitope presentation system that are obtained from the subject having the tumor (i.e., the first subject), are allogenic cells obtained from a cell bank or other source, and/or are derived from a second subject that is haploidentical to the first subject.

The immune competent cells obtained from a subject are, e.g., T-cells, B-cells, NK cells, and/or disposed within a peripheral blood mononuclear cell (PBMC) fraction of blood of the subject, are isolated exhausted T-cells and/or are grown from stem cells or precursor cells obtained from the first subject and/or from a second subject. In certain embodiments, the inventive method further includes a step of reactivating the isolated exhausted T-cells obtained from the first and/or second subject.

When the immune competent cells or cells for the neoepitope presentation system are allogenic, they are preferably matched to an HLA type from the first subject. For example, the immune competent cells are identified via a matrix that associates the neoepitope with at least one HLA sub-type from the subject.

In a further aspect of the invention, the neoepitope presentation system of the invention includes a subject- and tumor-specific neoepitope, a HLA-matched neoepitope, and a sequence-optimized neoepitope that binds to HLA. The neoepitope presentation system optionally also includes a second neoepitope, e.g., a tumor-associated neoepitope, a tumor-specific neoepitope and/or a subject and tumor-specific neoepitope. The neoepitope expression system includes, for example, a vector selected from the group consisting of a viral vector, a plasmid vector, a bacterial vector, and a non-episomal mammalian vector expressing at least one neoepitope for antigen delivery to desired cells for presentation. This is, for example, an adenovirus, and preferably the adenovirus has a deleted E2b gene. Another suitable viral vector is a lentivirus vector, as described by Dastagir, et al, 2017 (*Mol Ther Methods Clin Dev.;* 4: 27-38; Published online 2016 Dec. 24. doi: 10.1016/j.omtm.2016.12.002 or as described by *J Allergy Clin Immuno* 109 (6): 988-994.

In a yet further aspect, the neoepitope delivery system comprises an RNA or DNA for transfection, a synthetic neoepitope peptide, an expressed soluble neoepitope and/or the neoepitope that is coupled to a carrier. The carrier is, for example, an albumin. Further, the neoepitope presentation system optionally includes the neoepitope bound to an MHC-I or a MHC-II. In a still further aspect, the neoepitope in the neoepitope presentation system is displayed on a cell, e.g., via at least one of MHC I or MHC II. The cell is, for example, derived from the subject, and includes, e.g., an antigen presenting cell.

The step of triggering the immune response by contacting the immune competent cells also optionally includes also contacting the immune competent cells with an immune-stimulatory compound. In either method, the triggering is contemplated to be performed in any suitable art-known setting or apparatus, e.g., including in a culture medium and or in a suitable in vivo animal model. The culture medium for in vitro contacting can be included, for example, in a good manufacturing practice (GMP) in-a-box system. The system for in vivo contacting can be in a suitable animal model, e.g., a nude mouse model or zebrafish model, with implanted immune competent cells. In certain aspects, the immune competent cells are further contacted with a checkpoint inhibitor, e.g., a CTLA4 inhibitor or a PD-1 inhibitor.

The step of quantifying the triggering of the immune response includes one or more of the following options:
  measuring antibody-dependent cell-mediated cytotoxicity (ADCC) response,
  measuring release of at least one of granzyme, perforin, and a cytokine,
  taking an optical measurement of the immune competent cells, e.g., wherein the optical measurement method uses at least one of florescence and luminescence, and e.g., wherein the optical measurement measures at least one of a phase, a time-stretch, and LCI measurement, and also includes one or more of the following:
  measuring a multi-modal signature,
  measuring a pathway response,
  measuring in real-time in a continuous flow,
  measuring a time ramp up,
  measuring a trend,
  measuring at least one of a phosphorylation and a $Ca^{2+}$ flux,
  measuring a cell-killing metric,
  measuring a T-cell proliferation metric, and/or
  measuring cytokine secretion from an antigen-presenting cell, a natural killer cell, a Th1 cell, a Th2 cell, a Th17 cell, a regulatory T cell, an anergic T-cell, an exhausted T-cell, a $CD8^+$ T-cell, or a combination of any of the aforementioned cells.

In certain aspects, the inventive methods include a further step of processing the contacted immune competent cells to thereby enhance a measurement.

In certain additional aspects, the inventive method includes a further step of generating a validation measure as a function of a validation criterion. Preferably, the validation measure is subject specific and, for example, optionally calibrating a validation criterion.

Optionally, the inventive method includes a second step of quantifying the triggering, analogous to the first step.

Once the tested neoepitope is validated as stimulating a sufficient immune response in the test system, the inventive method is contemplated to include a further step of treating the cancer of the subject with the validated neoepitope. The validated neoepitope is also contemplated to be integrated or excluded from an anticancer therapeutic regime, depending on whether the neoepitope is successfully validated or not successfully validated by the inventive method.

The invention further includes a step of validating that the neoepitope exists on the tumor, e.g., by applying T-cell receptor information.

In a further aspect the inventive methods are contemplated to be conducted as an ex vivo method of validating a triggering of an immune response to a neoepitope of a first subject's tumor, comprising: obtaining an ex vivo sample of the first subject's tumor
  a) obtaining neoepitope sequence data from the sample of tumor of the first subject; b) obtaining ex vivo immune competent cells;
  c) using the neoepitope sequence data to generate an ex vivo neoepitope presentation system;
  d) triggering an immune response by contacting the immune competent cells with the neoepitope presentation system, ex vivo; and
  e) quantifying the triggering of the immune response from the contacted immune competent cells.

In this further aspect of the invention, the purpose of these methods is not treatment or diagnosis of a human, but rather validation of a therapeutic composition that was/is being generated. In addition, in this further aspect of the invention, all of the above described variations in the inventive method are contemplated to be available, but conducted ex vivo.

DETAILED DESCRIPTION

The invention provides methods for validating the anticipated effectiveness of one or more cancer neoepitopes to provoke an effective anticancer immune response against an individual subject's tumor or cancer by the steps including:
  a) obtaining neoepitope sequence data from the tumor of the subject, i.e., a first subject;
  b) obtaining immune competent cells from the subject, or allogenic cells, or from a second subject that is haploidentical to the first subject;
  c) using the neoepitope sequence data to generate a neoepitope presentation system;
  d) triggering an immune response by contacting the immune competent cells with the neoepitope presentation system; and
  e) quantifying the triggering of the immune response from the contacted immunecompetent cells.

It should be particularly appreciated that the inventive methods may be practiced prior to any treatment (and particularly immune therapy), or after surgery but prior to immune therapy, or prior to a second round of treatment (and particularly immune therapy).

In order to appreciate the present invention, the following terms are defined. Unless otherwise indicated, the terms listed below will be used and are intended to be defined as stated. Definitions for other terms can occur throughout the specification.

It is intended that all singular terms also encompass the plural, active tense and past tense forms of a term, unless otherwise indicated.

A "subject" or "patient" according to the invention is a human subject, such as a human patient with a tumor or cancer. In certain embodiments, the invention can also be applied in a veterinary practice to any vertebrate animal in need of such treatment. This includes, for example, a non-human primate, a canine, a feline, a porcine, an equine, and/or any other mammal. The term "subject" will also encompass a human or non-human who does not have a tumor or cancer, but who donates samples from which immune competent cells are obtained. In such an embodiment, the subject with the tumor is a first subject, and the donor subject is a second subject.

Neoepitope(s) as used herein are characterized as random mutations or pattern-type mutations in tumor cells that give rise to unique and tumor specific antigens. As such, it should be noted that exome and/or high-throughput genome sequencing allows for rapid and specific identification of patient or subject specific neoepitopes, particularly where the analysis also includes matched normal tissue of the same subject.

The term, "validating" as employed for the present invention, is defined as a method of confirming that a proposed anticancer immune therapy, such as a vaccine comprising one or more epitope, including a neoepitope, that is identified in a subject's cancer, will elicit an effective immune response in autologous immune cells isolated from the same subject. In other words, validation ensures that any immune response is useful in vivo, rather than being merely an ex vivo or in vitro phenomenon. The eliciting or triggering of an immune response can include measuring of an antibody-dependent cell-mediated cytotoxicity (ADCC) response, expansion of a specific cell population (e.g., reactive T-cells), and/or optical measurements on immune competent cells.

As used herein, the term "vector" refers, without limitation, to a nucleic acid molecule capable of expressing an encoded peptide, polypeptide or other nucleic acid to a host cell or other expression system. One type of vector is a "plasmid", which refers to a linear or circular double stranded DNA loop into which additional DNA segments can be ligated. Another type of vector is a viral vector, wherein additional DNA segments can be ligated into a suitable viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector.

Suitable plasmid vectors include, for example, pVAX1 as described by US20070269464 and WO2003057823; VR1012, pVAX1, pVC0396, pCMVkm2, pITR, pPJV7563, pWG4303, or pCOR, pDNAVACCUltra, as described by U.S. Pat. No. 9,737,620; and PNGVL4a, as described by U.S. Pat. No. 9,701,725.

However, the invention is intended to include such other forms of expression vectors, such as viral vectors (e.g., replication defective retroviruses, adenoviruses and adeno-associated viruses), lentivirus vectors, etc., which serve equivalent functions. Additionally, some viral vectors are capable of targeting certain types of cells, either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death. Adenovirus vectors, lentivirus vectors and plasmid vectors are all contemplated to be employed in delivering identified neoantigens to appropriate antigen presenting cells. Suitable viral vectors include, for example, an adenovirus, and preferably the adenovirus has a deleted E2b gene. Another suitable viral vector is a lentivirus vector, as described by Dastagir, et al, 2017 (*Mol Ther Methods Clin Dev.;* 4: 27-38; Published online 2016 Dec. 24. doi: 10.1016/j.omtm.2016.12.002 or as described by *J Allergy Clin Immuno* 109 (6): 988-994.

"Antigen presenting cells" (APCs) are cells that function to present antigens to the immune system, e.g., to helper T-cells, and include, for example, professional APC like macrophages, B cells and/or dendritic cells as well as non-professional APC like keratinocytes, fibroblasts, or other antigen-exposed cell types. Artificial APCs are also available for this function. An artificial APC is an art-known construct wherein an antigen of interest is bound to an MHC component to form an MHC antigen component, and the artificial APC also includes a liposome comprising a lipid bilayer, as described, for instance, by Albani, U.S. Pat. No. 7,807,377.

Co-incubating an antigen-presenting cell with a T-cell, such as a helper T-cell, means exposing an antigen-presenting cell to the T-cell under conditions such that the antigen-presenting cell can present an epitope of an antigen to the T-cell. The epitope can be a neoepitope. Presenting an antigen means an MHC Class I, MHC Class II, or non-classical MHC molecule on the APC contacting a T-cell or natural killer (NK) cell receptor. In some embodiments, the APC is infected by an adenovirus vector, optionally with an adenovirus with a deleted E2b gene. In other embodiments, the APC is transfected with mRNA encoding multiple neoepitopes in tandem, i.e., a polyepitope or polytope. In additional embodiments, synthetic neoepitopes or polytopes are incubated with an APC such that the APC takes up the neoepitope or polytope.

When the epitope is a polytope, the individual neoepitopes are separated by a suitable spacer (e.g., alanine residues for MHC Class I presentation and glycine or proline residues for MHC Class II presentation). Individual neoepitopes within a polytope may also be separated by glycine and proline residues for MHC Class II presentation. By "displayed" on a cell, it is meant that the neoepitope or polytope is disposed on the surface of a cell.

The contacting of an immune competent cell with a selected neoepitope, polytope, or neoepitope expression systems can be performed in vivo or in vitro. When performed in vitro the step of contacting the immune competent cells is conducted in an appropriate culture medium, including a culture system that functions as a "GMP in-a-box system," using the Austrianova's Cleanroom setup, or using a device as described by US20150065359, or using the culture systems taught by US20160108358, published on Apr. 21, 2016 and US20160083682, published on Mar. 24, 2016, or using a continuous culturing device as described by U.S. Pat. No. 9,220,731.

When performed in vivo, the step of contacting the immune competent cells is performed in an implant, such as an implant of cells that present the selected neoepitope, polytope, or neoepitope expression systems in the in vivo environment, e.g., in an animal xenograft system.

Alternatively, the methods of the invention are conducted entirely ex vivo, and the purpose of these methods is not treatment or diagnosis of a human, but rather validation of a therapeutic composition that was/is being generated.

Obtaining Neoepitope Sequence Data from a Subject's Tumor

A living tumor sample can be obtained from a subject having a tumor or cancer by any art-known method. For example, the tumor sample can be surgically removed during exploratory surgery as a biopsy sample. Alternatively, the tumor can be removed during surgical resection of a tumor mass, in whole or in part. In certain alternative embodiments, the tumor sample is acquired in the form of cells recovered from blood or other body fluids, e.g., as enriched circulating tumor cells (CTCs) by art-known methods. For example, circulating tumor cells can be obtained by subjecting the subject's blood or body fluid to one or more of dielectrophoresis, affinity separation, mass separation, FACS, LCI, and/or microfluidic cell sorting. The sorting can be conducted according to art-known methods and can include preferentially selecting CTCs that express a particular surface marker.

Once the tumor sample is obtained, it is analyzed to identify any neoepitopes that may be present and that may be a suitable target for anticancer immunotherapy. In more detail, a cancer neoepitope is, for example, one or more of a cancer-associated or cancer-specific peptide, a nucleic acid, a lipid, a sugar, and/or other type of molecule that the subject reacts to. A cancer neo-epitope is also a combination of a cancer-associated and/or a cancer-specific peptide, a nucleic acid, a lipid and/or a sugar. In certain embodiments, a cancer neoepitope is a cancer-associated or cancer-specific peptide, protein and/or nucleic acid identified by a genetic comparison between a cancer cell and a normal cell of a subject. In another embodiment, the neoepitope is an HLA-matched neoepitope.

Thus, in one embodiment, it is contemplated that prior to providing individualized anticancer treatment, a tumor biopsy is obtained from a subject in need thereof, and omics analysis is performed on the obtained tumor sample. In general, it is contemplated that the omics analysis includes whole genome and/or exome sequencing, RNA sequencing and/or quantification, and/or proteomics analysis by art-known methods. Preferred analytic methods include WGS (whole genome sequencing) and exome sequencing of both tumor and matched normal sample. Likewise, the computational analysis of the sequence data may be performed in numerous ways. In most preferred methods, however, analysis is performed in silico by location-guided synchronous alignment of tumor and normal samples as, for example, disclosed in US 2012/0059670A1 and US 2012/0066001A1 using BAM files and BAM servers. Of course, alternative file formats (e.g., SAM, GAR, FASTA, etc.) are also expressly contemplated herein.

In addition, RNA sequencing and/or quantification can be performed by any methods known in the art, and may use various forms of RNA. For example, preferred materials include mRNA and primary transcripts (hnRNA), and RNA sequence information may be obtained from reverse transcribed polyAtRNA, which is in turn obtained from a tumor sample and a matched normal (healthy) sample of the same subject. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis. Most typically, RNA quantification and sequencing are performed using qPCR and/or RT-PCR based methods, although other methods (e.g., solid phase hybridization-based methods) are also deemed suitable. Viewed from another perspective, transcriptomic analysis may be suitable (alone or in combination with genomic analysis) to identify and quantify genes having a cancer and/or subject specific mutation.

Similarly, proteomics analysis can be performed by numerous methods, and all known methods of proteomics analysis are contemplated herein. However, particularly preferred proteomics methods include antibody-based methods and mass spectroscopic methods (and especially selected reaction monitoring). Moreover, it should be noted that the proteomics analysis may not only provide qualitative or quantitative information about the protein per se, but may also include protein activity data where the protein has catalytic or other functional activity. Exemplary techniques for conducting proteome assays are described, for example, by U.S. Pat. Nos. 7,473,532 and 9,091,651.

Therefore, tumor-specific neoepitopes are identified against a matched normal sample of a subject, and preferably included in the analysis only if the neoepitope is due to a missense mutation and/or above a minimum expression level (e.g., at least 20%). Additionally, such filtering can be further refined by confirming high transmembraneous expression level of cancer neoepitopes. To facilitate computational analysis, it is contemplated that neoepitopes will be confined to relatively small fragments having a minimum size necessary for antibody binding (e.g., at least 5-6 amino acids) and a maximum size of 20 amino acids (and in some cases longer). Thus, suitable neoepitopes will preferably have a length of between 7-12 amino acids, for example, nine amino acids, including the changed amino acid.

Genomic analysis can be performed by any number of analytic methods. However, especially preferred analytic methods include exome and whole genome sequencing of both tumor and matched normal sample. Likewise, the computational analysis of the sequence data may be performed by numerous methods. However, in particularly preferred methods, analysis is performed in silico by location-guided synchronous alignment of tumor and normal samples as, for example, disclosed in US 2012/0059670A1 and US 2012/0066001A1 using BAM files and BAM servers. It should be noted that any language directed to a computer should be read to include any suitable combination of computing devices, including servers, interfaces, systems, databases, agents, peers, engines, controllers, or other types of computing devices operating individually or collectively. One should appreciate that the computing devices comprise a processor configured to execute software instructions stored on a tangible, non-transitory computer readable storage medium (e.g., hard drive, solid state drive, RAM, flash, ROM, etc.).

The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Identification of expression level can be performed by any art-known method. Preferred methods include quantitative RNA (hnRNA or mRNA) analysis and/or quantitative proteomics analysis. Most typically, but not necessarily, the threshold level for inclusion of neoepitopes will be an expression level of at least 20%, and more typically at least 50% as compared to matched normal, thus ensuring that the epitope is at least potentially 'visible' to the immune system. Thus, it is generally preferred that the omics analysis also includes an analysis of gene expression (transcriptomic analysis) to so help identify the level of expression for the gene with a mutation. Viewed from another perspective, transcriptomic analysis may be suitable (alone or in combination with genomic analysis) to identify and quantify genes having a cancer and subject specific mutation. There are numerous methods of transcriptomic analysis know in the art, and all of the known methods are deemed suitable for use herein. Taken the above into consideration, it should therefore be appreciated that a subject sample comprising DNA and RNA from tumor and matched normal tissue can be used to identify specific mutations and to quantify such mutations.

Neoepitopes obtained as described above may be subject to further detailed analysis and filtering using predefined structural and expression parameters, and/or sub-cellular location parameters. For example, it should be appreciated that neoepitope sequences are only retained provided they will meet a predefined expression threshold (e.g., at least 20%, 30%, 40%, 50%, or higher expression as compared to normal), or are identified as having a membrane associated location (e.g., are located at the outside of a cell membrane of a cell). Further contemplated analyses will include structural calculations that delineate whether or not a neoepitope is likely to be solvent exposed, presents a structurally stable epitope, etc. Further examples, methods, and neoepitopes are found in International applications WO2016/164833 (filed 8 Apr. 2016) and WO2016/172722 (filed 25 Apr. 2016), both incorporated by reference herein.

In a further embodiment, cancer neoepitopes are directly identified with the aid of advanced high sensitivity liquid chromatography mass spectroscopy (LC/MS), as described, for example, by Bassani-Sternberg et al., 2016 (Nature Communications 7, Article number: 13404 (2016); doi: 10.1038/ncomms13404).

Neoepitope Peptides and Antibodies

To obtain useful quantities of the neoepitope(s) identified above, it is contemplated that the epitope(s) identified above are prepared in vitro to yield a synthetic epitope, e.g., a synthetic peptide. There are numerous methods known in the art to prepare synthetic peptides, and all known methods are deemed suitable for use herein. For example, peptides with cancer neoepitope sequences can be prepared on a solid phase (e.g., using Merrified synthesis), via liquid phase synthesis, or from smaller peptide fragments. In some other aspects, peptides could also be produced by expression of a recombinant nucleic acid in a suitable host (especially where multiple neoepitopes are on a single peptide chain, optionally with spacers between neoepitopes or cleavage sites).

Therefore, the structure of the synthetic peptides corresponding to the neoepitope sequences may be $X-L_1-(A_n-L_2)_m-Q$, in which X is an optional coupling group or moiety that is suitable to covalently or non-covalently attach the synthetic peptide to a solid phase, $L_1$ is an optional linker that covalently links the synthetic peptide to a solid phase, or to the coupling group. $A_n$ is the synthetic peptide having the neoepitope sequence, with A being a natural (proteinogenic) amino acid and n is an integer between 7 and 30, and most typically between 7 and 11 or 15-25. $L_2$ is an optional linker that may be present, especially where multiple synthetic peptide sequences (identical or different) are in the construct, and m is an integer, typically between 1 and 30, and most typically between 2 and 15. Finally, Q is a terminal group which may be used to couple the end of the synthetic peptide to the solid phase (e.g., to sterically constrain the peptide) or to a reporter group (e.g., fluorescence marker) or other functional moiety (e.g., an affinity marker and/or an immune modulator molecule according to the present invention). Consequently, it should be noted that where the synthetic peptide is used for direct MHC-I binding, the overall length will be between 8 and 10 amino acids. Similarly, where the synthetic peptide is used for direct MHC-II binding, the overall length will be between 14 and 20 amino acids. On the other hand, where the synthetic peptide is processed in the cell (typically via proteasome processing) prior to MHC presentation, the overall length will typically be between 10 and 40 amino acids, with the changed amino at or near a central position in the synthetic peptide. Therefore, and viewed from a different perspective, the synthetic neoepitope may be a short single neoepitope sequence between 7-13 or between 15-25 amino acids, optionally with a linker between the peptide and a solid phase, or a concatemer of more than synthetic neoepitope where a linker is typically interposed between the individual synthetic neoepitopes.

For example, X could be a non-covalent affinity moiety (e.g., biotin) that binds a corresponding binding agent (e.g., avidin) on the solid phase, or a chemical group (with or without spacer) that reacts with the N- or C-terminal amino or carboxyl group of the peptide, or a selectively reactive group (e.g., iodoacetyl or maleimide group) that reacts with a sulfhydryl group in the peptide or linker $L_1$. $L_1$ may be used to increase the distance of the synthetic peptide from the solid phase and will therefore typically comprise a flexible linear moiety (e.g., comprising glycol groups, alkoxy groups, glycine, etc.) having a length of equivalent to between about 2-20 carbon-carbon bonds (e.g., between 0.3 nm and 3 nm). Of course, it should also be appreciated that the synthetic peptide may use the solid phase on which the peptide was produced and as such not require a separate coupling group or linker.

Depending on the particular synthetic peptide and coupling method, it should be appreciated that the nature of the solid phase may vary considerably, and all known solid phases for attachment of peptides are deemed suitable for use herein. For example, suitable solid phases include agarose beads, polymer beads (colored or otherwise individually addressable), wall surfaces of a well in a microtiter plate, paper, nitrocellulose, glass, etc. The person of ordinary skill in the art will be readily appraised of a suitable choice of solid phase and attachment chemistry. In further preferred aspects, it is also noted that the solid phase will generally be suitable for protocols associated with phage display methods such as to allow peptides presented on a phage (or other scaffold carrier) to reversibly bind to the solid phase via the synthetic peptide. In still further contemplated uses, it should also be recognized that the solid phase may be a carrier protein used in vaccination (e.g., albumin, KLH, tetanus toxoid, diphtheria toxin, etc.), particularly where the synthetic protein is used as a vaccine in a mammal or as an immunogenic compound in a non-human mammal for antibody production. Likewise, the synthetic protein may also be used as a vaccine or immunogenic compound without any carrier.

To obtain an antibody that binds to the identified neoepitope, the above described synthetic peptide is employed as an antigen, with a suitable adjuvant and/or an expression vector encoding a multi epitope construct, to elicit an immune response in a suitable subject human or other mammalian immunological system.

Obtaining Immune Competent Cells

Autologous immune cells contemplated to be isolated from the subject include, for example, T-cells, B-cells, and/or NK cells, or other immune competent cells present within a peripheral blood mononuclear cell (PBMC) fraction of blood of the first or second subject. PBMC cells are well known in the art as the cells present in the buffy coat of a tube of centrifuged blood, and are also obtainable by Ficoll-Paque™ density gradient fractionation (reagents available from GE Healthcare). PBMC cell populations include, e.g., lymphocytes (T-cells, B cells, and NK cells), monocytes, and/or dendritic cells. Most preferably, immune competent cells will be freshly prepared or propagated from whole blood of the subject. However, in alternative aspects, the immune competent cells may also be prepared or propagated from previously cryopreserved blood cells of the first subject or from cryopreserved cells of a second subject. To that end, it should be appreciated that the prepared or propagated immune competent cells may not only be employed in the validation process, but also as therapeutic (adjunct) agent, for example, where the subject's own supply of immune competent cells is insufficient (e.g., due to prior chemotherapy).

T-cells, B-cells, NK and dendritic cells can be isolated from the tissues and/or, peripheral blood of a subject, by art-known methods. T-cells can be isolated from a subject e.g., as described by Johnson et al., US20070141034. B-cells can be isolated from a subject, e.g., as described by Allison et al., US 20140287952, NK cells can be isolated from a subject, e.g., as described by Alici, U.S. Pat. No. 8,877,182. Dendritic cells can be isolated from a subject, e.g., as described by Cohen et al., U.S. Pat. No. 5,643,786, Crawford et al., U.S. Pat. No. 6,589,526 and/or Moore et al., US20060280727.

In yet another example, suitable NK cells may be obtained from previously established therapeutic cell lines, or may be derived from cell lines which are well known in the art. For example, suitable cell lines include NK92 cells (e.g., commercially available from Nantkwest, 9920 Jefferson Blvd. Culver City, CA 90232) or TALL 104 cells (e.g., commercially available from ATCC, CRL-11386, 10801 University Boulevard, Manassas, VA 20110 USA).

In another embodiment, the T-cells are exhausted T-cells. An "exhausted T-cell" is a T-cell is characterized by the stepwise and progressive loss of T-cell functions. Exhausted T-cells may be reactivated with IL-2, IL-7, IL-15, and IL-21. The term "exhaustion," with reference to T-cell exhaustion, is a state of T-cell dysfunction that arises from sustained TCR signaling that occurs during many chronic infections, e.g., hepatitis B virus, hepatitis C virus and human immunodeficiency virus infections, and from cancer. T-cell exhaustion is distinguished from anergy in that it arises not through incomplete or deficient signaling, but from sustained signaling. It is defined by poor effector function, sustained expression of inhibitory receptors and a transcriptional state distinct from that of functional effector or memory T-cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.) ((US20160317632).

In a further embodiment, exhausted T-cells are isolated by art-known methods, and tested for their capacity for reactivation. Alternatively, exhausted T-cells are generated from stem cell precursors. Another source of exhausted T-cells are cells from HLA-matched donors from a cell bank.

For example, as described by Blackburn, et al., 2008, PNAS, 105(39): 15016-15021, CD8 T-cells are purified by magnetic beads (Miltenyi Biotec) tagged with markers specific for exhausted T-cells, or by FACS sorting. CD8 T-cells carrying markers specific for exhaustion, e.g., $PD1^{H1}$ and $PD1^{Int}$ markers are then separated on magnetic beads tagged with appropriate antibody or other binders for the art known markers of T-cell exhaustion, and/or tagged for fluorescence activated cell sorting (FACS) by appropriate fluorescent labeled marker specific probes.

T-cell reactivation can be assessed by increase in cytotoxic activity and/or increased cell division, or via other measures of antigen-specific reactivity (e.g., mixed lymphocyte reaction, biomolecule production, decreases in expression of T-cell markers associated with T-cell exhaustion, and increases in expression of T-cell markers associated with T-cell activation, etc.). For example, antigen-specific reactivity can be assessed by loading an antigen-presenting cell with an antigen and contacting a T-cell of interest with the loaded antigen-presenting cell. Antigen-specific reactivity can also be assessed using tetramers and dextramers with flow cytometry. The biomolecules produced can be interleukins such as IL-2, IL-4, and IL-12, interferons such as IFN-α, IFN-β, and IFN-γ, or other molecules such as tumor necrosis factor-α, (TNF-α), TNF-β, and granzyme B. The T-cell markers whose expression is decreased can be PD-1, Tim-3, LAG-3, CD44, CD43, CD69, CD127, CD62L, and BLIMP-1. The T-cell markers whose expression is increased can be the T-cell receptor, CD11, CD28, CTLA-4, the IL-2 receptor, the IL-7 receptor, the IL-15 receptor, and the IL-21 receptor.

In yet another embodiment of the invention, immune competent cells are grown from subject stem cells or precursor cells. The stem cells can be derived from bone marrow, peripheral blood, adipose tissue, biopsy samples, and the mesenchyme. The stem cells can be dedifferentiated into embryonic stem cells or pluripotent stem cells. The stem cells can also be cultured directly from the aforementioned sources.

Thus, T-cells reactive to one or more neoepitopes are isolated from a subject and can be tested for reactivity against antigen-presenting cells. Reactivity to an epitope can be assessed by exposing antigen-presenting cells to the neoepitopes directly, exposing an antigen-presenting cell to a vector either bearing the neoepitopes, or exposing an antigen-presenting cell to a vector capable of expressing the neoepitopes. During, or after, the exposure, T-cell reactivity can be assessed by contacting a T-cell with the antigen-presenting cell.

In additional embodiments, the immune competent cells are allogenic cells, optionally matched to an HLA type from the subject and/or obtained from a cell bank and are matched to an HLA type from the subject.

The percentage of identity between the HLA type of the allogenic cells and the HLA type of the subject may be 100%, 99%, 98%, 97%, 96%, 95%, 90%, 85%, 80%, or 75%. The HLA types at the major histocompatibility complex can be 100%, 99%, 98%, 97%, 96%, 95%, 90%, 85%, 80%, or 75% identical and the HLA types at the minor histocompatibility complex may be 100%, 99%, 98%, 97%, 96%, 95%, 90%, 85%, 80%, or 75% identical.

In a further embodiment, suitable immune competent cells are identified via a matrix that associates the neoepitope with at least one HLA sub-type from the subject. For example, the subject's MHC-I and MHC-II subtypes may be listed to at least four or at least six digits depth for each subtype, while MHC-I and MHC-II subtypes of potentially suitable immune competent cells are also indexed to the same or similar depth. Appropriate immune competent cells may then be selected from such matrix using a match score that is based on a degree of identity of MHC-I and MHC-II subtypes between the subject's cells and the potentially suitable immune competent cells.

Reactivating Exhausted T-Cells

An "exhausted T-cell" is a T-cell is characterized by the stepwise and progressive loss of T-cell functions. Exhausted T-cells are reactivated by contacting the exhausted T-cells with one or more of IL-2, IL-7, IL-15, and/or IL-21. The term "exhaustion," with reference to T-cell exhaustion, is a state of T-cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T-cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.) ((US20160317632). Reactivation of exhausted T-cells can be assessed as described above.

Using Neoepitope Sequence Data to Generate a Neoepitope Presentation System

A neoepitope presentation system is generated by one of several methods known to the art. In one example, the MHC complex is identified by clonal analysis of antigen-presenting cells, and e.g., the neoepitope is expressed within an antigen-presenting cell. The antigen-presenting cell can also be contacted with a neoepitope, such that the neoepitope is internalized within the antigen-presenting cell. A population of antigen-presenting cells can also be diluted and dispensed into wells such that, on average, each well contains one antigen-presenting cell. The population of antigen-presenting cells can be a population of immortalized antigen-presenting cells. The dispensed antigen-presenting cells can be contacted with a population of T-cells, and the wells containing the dispensed population of antigen-presenting cells can be assessed for T-cell activation. Wells exhibiting T-cell activation can be identified and the MHC molecules expressed by the antigen-presenting cell can be determined by molecular techniques well known in the art.

Immunotherapy treatment success requires neoepitopes to be presented via the major histocompatibility complex (MHC complex). Thus, it should be appreciated that the neoepitopes or their precursors must not only be suitable for intracellular processing via appropriate mechanisms (e.g., proteasomal cleavage, formation of TAP complex, vesicular transport, etc.) but also have a minimum affinity to the subject's human leukocyte antigen type (HLA-type). Therefore, it is generally preferred that the HLA-type of the subject be determined, either using conventional wet-lab methods, or via in silico methods as further described in more detail below. Viewed from a different perspective, it should be appreciated that identified neoepitopes may be further qualified for prediction of treatment outcome by ascertaining their binding to the subject specific MHC-type.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types as is shown in more detail below. In short, a subject's HLA-type is ascertained (using wet chemistry or in silico determination), and a structural solution for the HLA-type is calculated or obtained from a database, which is then used as a docking model in silico to determine binding affinity of the neoepitope to the HLA structural solution. Suitable in silico prediction methods of the HLA-type of a subject especially include those described in U.S. provisional applications 62/209,858 (filed 25 Aug. 2015), which is incorporated by reference herein. Suitable systems for determination of binding affinities include the NetMHC platform (see e.g., Nucleic Acids Res. 2008 Jul. 1; 36 (Web Server issue): W509-W512.). Neoepitopes with high affinity (e.g., less than 100 nM, less than 75 nM, less than 50 nM) against the previously determined HLA-type are then selected.

Once subject and tumor specific neoepitopes and HLA-type are identified, computational analysis can be performed by docking neoepitopes to the HLA and determining best binders (e.g., lowest $K_D$, for example, less than 50 nM). It should be appreciated that such an approach will not only predict microsatellite instable (MSI) cancers, but also identify neoepitopes that are most likely to be presented on a cell and therefore most likely to elicit an immune response with therapeutic effect. Of course, it should also be appreciated that such identified HLA-matched neoepitopes can be biochemically validated in vitro.

All of the preceding steps are performed in silico. Preceding steps will likely provide more than one, more typically more than ten, or more than 100 candidate neoepitopes and suitable choices to be validated. Next steps include preparing of neoepitopes or vehicles for delivery of the neoepitopes as a vaccine. For example, viral, bacterial, or yeast expression systems for in vivo expression of neoepitopes, and/or in vitro generation of synthetic peptides having neoepitope sequences.

Optionally, the neoepitope presentation system further includes at least one additional neoepitope, e.g., a second, third, fourth or fifth, or more, neoepitope, such as a tumor-associated neoepitope, a tumor-specific neoepitope or subject and/or tumor specific neoepitope.

Contacting the Immune Competent Cells with the Neoepitope Presentation System

The triggering step is conducted by exposing the epitope of interest to an antigen-presenting cell by co-incubating the epitope with the antigen-presenting cell. Optionally, the step of triggering includes a second triggering step.

The neoepitopes are contemplated to be presented to the immune competent cells as, e.g., a free peptide, in suspension, or as a soluble expressed neoepitope, as a neoepitope combined with a suitable carrier, adjuvant or enhancer. The neoepitopes are also contemplated to be displayed as expressed by mRNA, plasmid vectors, viral systems such as adenovirus vectors, decoration of MHC, expression on cells of the subject, and/or expressed on APCs. One mode of expression is via mRNA in a cellular or acellular system. Another mode of expression is via a viral system, such as, but not exclusive to, a viral vector, an adenovirus that from which the E2b gene is optionally deleted, and Ad5.

A further mode of expression is decoration, i.e., isolated or cell bound MHC is associated in vitro with the neoepitope, such that the neoepitope is bound to the MHC without intracellular processing. In some modes of decoration, the neoepitope/MHC complex can be present on a polymer backbone. A fluorochrome can also be present on the backbone. In other modes of decoration, the neoepitope is present at the tip of the Fab fragment of an immunoglobulin molecule. The immune competent cell can also optionally be contacted with a checkpoint inhibitor, such as, e.g., CTLA4 inhibitor or a PD-1 inhibitor. The immune competent cell can further be contacted with an immune-stimulatory compound, such as, e.g., a cytokine, such as IL-2, or a Fc fusion protein such as CD80-Fc or CD86-Fc.

An additional mode of expression is displaying the epitope on a subject's cells or on a donor's cells. The epitope may be expressed as a fusion protein with another molecule expressed at the cell surface.

Various antigen presentation systems exist. For example, neoepitopes expressed within a cell can be presented on MHC Class I molecules. Neoepitopes can also be derived extracellularly and presented on MHC Class II molecules. Neoepitopes expressed within a cell can also be presented on MHC Class II molecules. Neoepitopes can also be presented to B-cells as intact antigens.

Neoepitope presentation can be identified using a number of techniques. For example, the neoepitope can be linked to another protein such as albumin or keyhole limpet hemocyanin, a bead such as a microbead or a paramagnetic bead, or a synthetic polymer. T-cell responses can then be assessed by direct binding to the protein-linked neoepitope, the bead-linked neoepitope, or synthetic polymer-linked neoepitope. T-cell responses can also be assessed by exposing an antigen-presenting cell to the protein-linked neoepitope, the bead-linked neoepitope, or synthetic polymer-linked neoepitope, and allowing the antigen-presenting cell to present the neoepitope on the surface of the antigen-presenting cell. The antigen-presenting cell may be a professional antigen-presenting cell such as a dendritic cell or another cell type capable of antigen presentation. The antigen-presenting cell may be HLA matched for neoepitope expression.

Quantifying Triggering of the Immune Response from the Contacted Immune Competent Cells Quantifying the triggering of an immune response can be achieved by selecting an assay for triggering with an objective output. An objective outcome can be the incorporation of tritiated thymidine, the increase in number of immune competent cells, an ELISA or cell-proliferation assay for the presence of an immune reactive molecule, or flow cytometry.

It is contemplated that the invention includes methods of quantifying the triggering of the immune response, by any art-known methods. The method of quantifying is conducted in one or more steps, e.g., from 1 to 10, or more steps. In particular, the method includes from 1 to 5 or from 1 to 2 steps.

For example, the method of quantifying the triggering of the immune response includes measuring antibody-dependent cell-mediated cytotoxicity (ADCC), measuring release of at least one of granzyme, perform, and/or a cytokine. Measurements include taking an optical measurement, e.g., florescence and luminescence, of the immune competent cells. The optical measurement, includes, for example, at least one of a phase, a time-stretch, LCI measurement, and/or a multi-modal signature.

The method of quantifying the triggering of the immune response is also contemplated to include measuring a pathway response.

In addition, the step of quantifying the triggering of the immune response includes measuring in real-time in a continuous flow and/or measuring a time ramp up and/or a trend.

In another alternative, the step of quantifying the triggering of the immune response includes:
measuring at least one of a phosphorylation and a $Ca^{2+}$ flux and/or measuring a cell-killing metric,
measuring a T-cell proliferation metric,
measuring cytokine secretion,
processing the contacted immune competent cells to thereby enhance a measurement.
generating a validation measure as a function of a validation criterion, and/or
calibrating a validation criterion, that is optionally subject-specific.

What is claimed is:

1. A method of validating a therapeutic composition comprising a neoepitope of a first subject's tumor by confirming ex vivo a triggering of an immune response to the neoepitope of the first subject's tumor, comprising:
   a) obtaining neoepitope sequence data from the tumor of the first subject;
   b) obtaining immune competent cells from peripheral blood of the first subject or obtaining immune competent cells from peripheral blood of a second subject, wherein the immune competent cells are isolated exhausted T-cells, and wherein the immune competent cells of the second subject are matched to an HLA type of the first subject;
   c) using the neoepitope sequence data to generate a neoepitope presentation system comprising a dendritic cell or macrophage as an antigen presenting cell wherein the antigen presenting cell recombinantly expresses and intracellularly processes one or more neoepitopes encoded by the neoepitope sequence data of the first subject for antigen presentation on the antigen presenting cell;
   d) triggering ex vivo an immune response against the first subject's tumor by contacting the immune competent cells with the neoepitope presentation system; and
   e) confirming the triggering of the immune response in the first subject's tumor from the contacted immune competent cells.

2. The method of claim 1, wherein the immune competent cells are obtained from the second subject, and wherein the second subject is haploidentical to the first subject.

3. The method of claim 1, further comprising a step of reactivating the isolated exhausted T-cells.

4. The method of claim 1, wherein the immune competent cells are grown from stem cells or precursor cells obtained from the first subject or the second subject and wherein the second subject is haploidentical to the first subject.

5. The method of claim 1, wherein the immune competent cells are identified via a matrix that associates the neoepitope with at least one HLA sub-type from the subject.

6. The method of claim 1, wherein the neoepitope in the neoepitope presentation system comprises a subject- and tumor-specific neoepitope, or an HLA-matched neoepitope.

7. An ex vivo method of validating a therapeutic composition comprising a neoepitope of a first subject's tumor by confirming triggering of an immune response to the neoepitope of the first subject's tumor, comprising: obtaining an ex vivo sample of the first subject's tumor,
   a) obtaining neoepitope sequence data from the sample of tumor of the first subject;
   b) obtaining ex vivo immune competent cells from peripheral blood of the first subject or obtaining ex vivo immune competent cells from peripheral blood of a second subject, wherein the immune competent cells are isolated exhausted T-cells, and wherein the immune competent cells of the second subject are matched to an HLA type of the first subject;
   c) using the neoepitope sequence data to generate an ex vivo neoepitope presentation system comprising a dendritic cell or macrophage as an antigen presenting cell of the first subject wherein the antigen presenting cell recombinantly expresses and intracellularly processes one or more neoepitopes encoded by the neoepitope sequence data for antigen presentation on the antigen presenting cell;

d) triggering an immune response against the first subject's tumor by contacting the immune competent cells with the neoepitope presentation system, ex vivo; and e) confirming the triggering of the immune response against the first subject's tumor from the contacted immune competent cells.

8. The method of claim 7, wherein the immune competent cells are obtained from the second subject, and wherein the second subject is haploidentical to the first subject.

9. The method of claim 7, further comprising a step of reactivating the isolated exhausted T-cells.

10. The method of claim 7, wherein the immune competent cells are grown ex vivo from stem cells or precursor cells obtained from the first subject or the second subject, and wherein the second subject is haploidentical to the first subject.

11. The method of claim 7, wherein the immune competent cells are identified ex vivo via a matrix that associates the neoepitope with at least one HLA sub-type from the subject.

* * * * *